United States Patent
Sundaram et al.

(10) Patent No.: US 8,039,619 B2
(45) Date of Patent: *Oct. 18, 2011

(54) PROCESS FOR PREPARING (2R,3S/2S,3R)-2-(2,4-DIFLUOROPHENYL)-3-(5-FLUORO-PYRIMIDIN-4-YL)-1-(1H-1,2,4-TRIAZOL-1-YL)BUTAN-2-OL

(75) Inventors: Venkataraman Sundaram, Hyderabad (IN); Venkata Bhaskara Rao Uppala, Hyderabad (IN); Surya Prabhakar Akundi, Hyderabad (IN); Venkateswarlu Muvva, Hyderabad (IN); Vijayawardhan Chitta, Warangal (IN); Alekhya Donthula, Secunderabad (IN); Manoj Ramesh Kharkar, Hyderabad (IN); Surya Narayana Devarakonda, Hyderabad (IN); Subba Reddy Peddireddy, Hyderabad (IN)

(73) Assignees: Dr. Reddy's Laboratories Limited, Hyderabad, Andhra Pradesh (IN); Dr. Reddy's Laboratories, Inc., Bridgewater, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/797,790

(22) Filed: Jun. 10, 2010

(65) Prior Publication Data

US 2010/0292473 A1    Nov. 18, 2010

Related U.S. Application Data

(63) Continuation of application No. 11/721,697, filed as application No. PCT/US2005/044867 on Dec. 13, 2005.

(60) Provisional application No. 60/635,783, filed on Dec. 14, 2004, provisional application No. 60/684,667, filed on May 26, 2005.

(51) Int. Cl.
    *C07D 403/10* (2006.01)
(52) U.S. Cl. ...................................................... 544/333
(58) Field of Classification Search ................... 544/333
    See application file for complete search history.

(56) References Cited

U.S. PATENT DOCUMENTS

| 5,278,175 A | 1/1994 | Ray et al. |
| 5,567,817 A | 10/1996 | Ray et al. |
| 6,586,594 B1 | 7/2003 | Butters et al. |

FOREIGN PATENT DOCUMENTS

| CN | 1488629 A | 4/2004 |
| WO | 2007/013096 A1 | 2/2007 |

OTHER PUBLICATIONS

A. Goho, "Tricky Business," Science News, vol. 166, No. 8, pp. 122-123 (Aug. 2004).
Paul Rylander, "Catalytic Dehydrohalogenation" in Catalytic Hydrogenation in Organic Synthesis, Academic Press, New York, p. 235-250, 1979.
Wikipedia. Hydrogenation [online] [retrieved on Mar. 2, 2011]. Retrieved from the Internet: <http://en.wikipedia.org/wiki/Hydrogenation>, page was last modified on Feb. 28, 2011 at 00:17.

*Primary Examiner* — Venkataraman Balasubramanian
(74) *Attorney, Agent, or Firm* — Robert A. Franks; Thomas C. McKenzie; Balaram Gupta

(57) ABSTRACT

Voriconazole is prepared by a process comprising condensing 1-(2,4-difluorophenyl)-2-(1H-1,2,4-triazole-1-yl)ethanone with 4-chloro-6-ethyl-5-fluoropyrimidine, in a ketone, ether, aliphatic hydrocarbon, or aromatic hydrocarbon solvent, to give (2R,3S/2S,3R)-3-(4-chloro-5-fluoropyrimidin-6-yl)-2-(2,4-diflurophenyl)-1-(1H-1,2,4-triazole-1-yl)butan-2-ol.

10 Claims, 7 Drawing Sheets

PROCESS FOR PREPARING (2R,3S/2S,3R)-2-(2,4-DIFLUOROPHENYL)-3-(5-FLUORO-PYRIMIDIN-4-YL)-1-(1H-1,2,4-TRIAZOL-1-YL)BUTAN-2-OL

INTRODUCTION TO THE INVENTION

The present invention relates to processes for the preparation of voriconazole and its polymorphs. More specifically, the invention provides a process for the preparation of pure voriconazole, substantially free from impurities. The invention also relates to crystalline forms A and B of voriconazole as well as its amorphous form. The invention further relates to processes for the preparation of the different forms of voriconazole. Voriconazole has the chemical name (2R,3S)-2-(2,4-diflurophenyl)-3-(5-fluoropyrimidin-4-yl)-1-(1H-1,2,4-triazol-1-yl)-butan-2-ol and is represented by the structural Formula I.

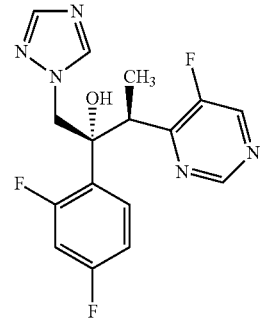

Formula I

Voriconazole is used for the treatment of invasive aspergilli; treatment of fluconazole-resistant, severe, invasive candida infections (including *C. krusei*); treatment of severe fungal infections with *scedosporium* spp. and *Fusarium* spp. Its commercially available embodiment is sold as VFEND™ in the form of an injectable formulation (200 mg per vial), solid oral formulations as 50 mg and 200 mg tablets and an oral suspension containing 200 mg of voriconazole/5 ml.

U.S. Pat. Nos. 5,278,175 and 5,567,817 disclose voriconazole, its pharmaceutically acceptable salts, pharmaceutical compositions comprising voriconazole and their use in the treatment of fungal infections. They also disclose a process for the preparation of voriconazole, which can be depicted by Scheme 1.

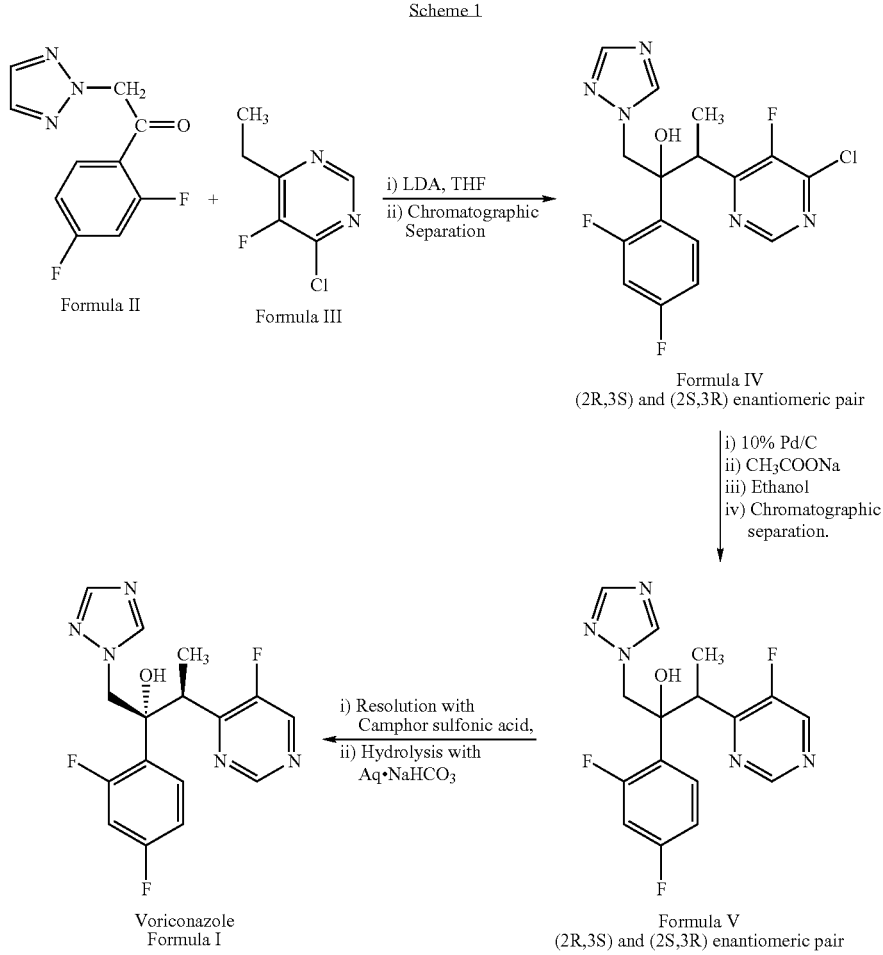

Scheme 1

In brief, the process includes the reaction of 1-(2,4-difluorophenyl)-2-(1H-1,2,4-triazole-1-yl)ethanone of Formula II with 4-chloro-6-ethyl-5-fluoropyrimidine of Formula III, in the presence of lithium diisopropylamide and in a tetrahydrofuran medium, to yield 3-(4-chloro-5-fluropyrimidin-6-yl)-2-(2,4-difluorophenyl)-1-(1H-1,2,4-triazole-1-yl)butan-2-ol as a residue. Column chromatography of the residue on silica using 3:2 ethyl acetate/diethyl ether as the eluant, first gave, after combination and evaporation of appropriate fractions and trituration with diethyl ether, a 2R,3S and 2S,3R enantiomeric pair of 3-(4-chloro-5-fluropyrimidin-6-yl)-2-(2,4-difluorophenyl)-1-(1H-1,2,4-triazole-1-yl)butan-2-ol of Formula IV, with a 12% yield. This, on hydrogenation with a 10% Pd/C catalyst in ethanol, in the presence of sodium acetate, followed by flash chromatographic separation yields (2R,3S/2S,3R)-2-(2,4-difluorophenyl)-3-(5-fluoro pyrimidin-4-yl)-1-(1H-1,2,4-triazol-1yl) butan-2-ol of Formula V. The compound of Formula V on resolution with R-(−)-10-camphor sulfonic acid in methanol gives a corresponding camphorsulfonate•0.5 methanol, which on hydrolysis with aqueous sodium bicarbonate solution gives voriconazole of Formula I.

The aforementioned process involves the chromatographic separation of a 2R,3S and 2S,3R enantiomeric pair from the residue containing four possible enantiomers of the intermediate compound of Formula IV, leading to poor yields. The process also uses palladium on charcoal as a catalyst in the reaction for preparation of Formula V and involves chromatographic purification, resulting in a process that is expensive and difficult to operate on an industrial scale.

U.S. Pat. No. 6,586,594 discloses a process for the preparation of voriconazole, which comprises condensing 1-(2,4-difluorophenyl)-2-(1H-1,2,4-triazol-1-yl)ethanone of formula II with 6-(1-bromoethyl)-2,4-dichloro-5-fluoropyrimidine in the presence of zinc powder, lead powder, and iodine in tetrahydrofuran to give the compound of Formula IV. This compound on reduction using a 10% Pd/C (palladium on carbon) catalyst followed by resolution with R-(−)-camphor-10-sulphonic acid resulted in the formation of voriconazole, which was isolated in isopropanol. The product recovered from this process appears to correspond with the crystalline form of voricanazole identified below as "Form B."

This process also involves the use of toxic and/or expensive reagents such as zinc, lead, iodine, and Pd/C resulting in a process that is expensive and difficult to operate on an industrial scale.

There is always a need for newer routes of synthesis of commercially important pharmaceutically active compounds, especially routes that are commercially feasible, using reactants and conditions that are non-toxic, cost effective, and environmentally friendly.

Regulatory authorities internationally desire to have all possible polymorphic forms of a new drug substance identified prior to approval of a product containing the drug. However, as is well known in the art, the existence of polymorphic forms of any given compound cannot be predicted, and there is no standard procedure for proceeding to make a previously unknown polymorphic form. Even after a polymorph has been identified, there is no possibility of predicting whether any additional forms will ever be discovered. This situation has been the subject of recent articles, including A. Goho, "Tricky Business," Science News, Vol. 166, No. 8, pages 122-123(August 2004). So also, it is impossible to predict whether it would be possible to obtain an amorphous or other form of a new drug substance and what would be its stability. There is thus also a need to prepare and identify different crystalline and amorphous forms of such compounds.

Consequently, it would be a significant contribution to the art to provide newer and improved processes for the synthesis of a commercially important compound such as voriconazole, its different polymorphic forms and its amorphous form, pharmaceutical formulations containing these forms, and methods of use therefor.

SUMMARY OF THE INVENTION

The present invention relates to processes for the preparation of voriconazole and its polymorphs. The invention also relates to novel crystalline form A of voriconazole, as well as to its amorphous form.

In one aspect, the invention provides a process for preparing voriconazole, comprising condensing 1-(2,4-difluorophenyl)-2-(1H-1,2,4-triazole-1-yl)ethanone with 4-chloro-6-ethyl-5-fluoropyrimidine, in a ketone, ether, aliphatic hydrocarbon, or aromatic hydrocarbon solvent, to give (2R, 3S/2S,3R)-3-(4-chloro-5-fluoropyrimidin-6-yl)-2-(2,4-difluorophenyl)-1-(1H-1,2,4-triazole-1-yl)butan-2-ol.

An aspect of the present invention relates to a process for the preparation of voriconazole of Formula I comprising the steps of:
a) condensing 1-(2,4-difluorophenyl)-2-(1H-1,2,4-triazole-1-yl)ethanone with 4-chloro-6-ethyl-5-fluoropyrimidine to give (2R,3S/2S,3R)-3-(4-chloro-5-fluropyrimidin-6-yl)-2-(2,4-difluorophenyl)-1-(1H-1,2,4-triazole-1-yl)butan-2-ol;
b) hydrogenating (2R,3S/2S,3R)-3-(4-chloro-5-fluropyrimidin-6-yl)-2-(2,4-difluorophenyl)-1-(1H-1,2,4-triazole-1-yl)butan-2-ol to give (2R,3S/2S,3R)-2-(2,4-difluorophenyl)-3-(5-fluoro pyrimidin-4-yl)-1-(1H-1,2,4-triazol-1yl) butan-2-ol;
c) resolving (2R,3S/2S,3R)-2-(2,4-difluorophenyl)-3-(5-fluoro pyrimidin-4-yl)-1-(1H-1,2,4-triazol-1yl)butan-2-ol to afford a diastereomeric salt; and
d) converting the diastereomeric salt to voriocnazole.

In another aspect, the present invention provides substantially pure voriconazole free from impurities and a process for preparation thereof.

According to this embodiment of the invention, voriconazole containing low concentrations of any one or more of the following impurities as determined by HPLC, is provided:
a) 2,4-difluro-1H-1-yl-1,2,4-triazole acetophenone;
b) 6-ethyl-5-fluoro pyrimidine;
c) 4-chloro-6-ethyl-5-fluro pyrimidine;
d) 6-[(1-(5-fluoro pyrimidinyl)-6-ethyl]-4-chloro-5-fluoro pyrimidine
e) (2R,3S/2S,3R)-3-(4-chloro-5-fluoropyrimidin-6-yl)-2-(2,4-difluorophenyl)-1-(1H-1,2,4-triazol-1-yl)butan-2-ol;
f) (2R,3R/2S,3S)-3-(4-chloro-5-fluoropyrimidin-6-yl)-2-(2,4-difluorophenyl)-1-(1H-1,2,4-triazol-1-yl)butan-2-ol;
g) (2R, 3R/2S, 3S)-2-(2,4-difluorophenyl)-3-(5-fluoropyrimidin-4-yl)-1(1H-1,2,4-triazol-1-yl)butan-2-ol; and
h) (2S,3R)-2-(2,4-difluorophenyl)-3-(5-fluoropyrimidin-4-yl)-1(1H-1,2,4-triazol-1-yl)butan-2-ol.

In yet another aspect, the present invention provides crystalline Form A of voriconazole.

In a further aspect, the present invention provides processes for the preparation of crystalline Form A and Form B of voriconazole.

In a still further aspect, the present invention provides amorphous voriconazole either alone or in combination with a pharmaceutically acceptable carrier and a process for the preparation thereof.

In another aspect the present invention provides a pharmaceutical composition containing one or more of crystalline form A, crystalline form B and amorphous voriconazole, and processes for the preparation thereof.

DETAILED DESCRIPTION

Figure 1:
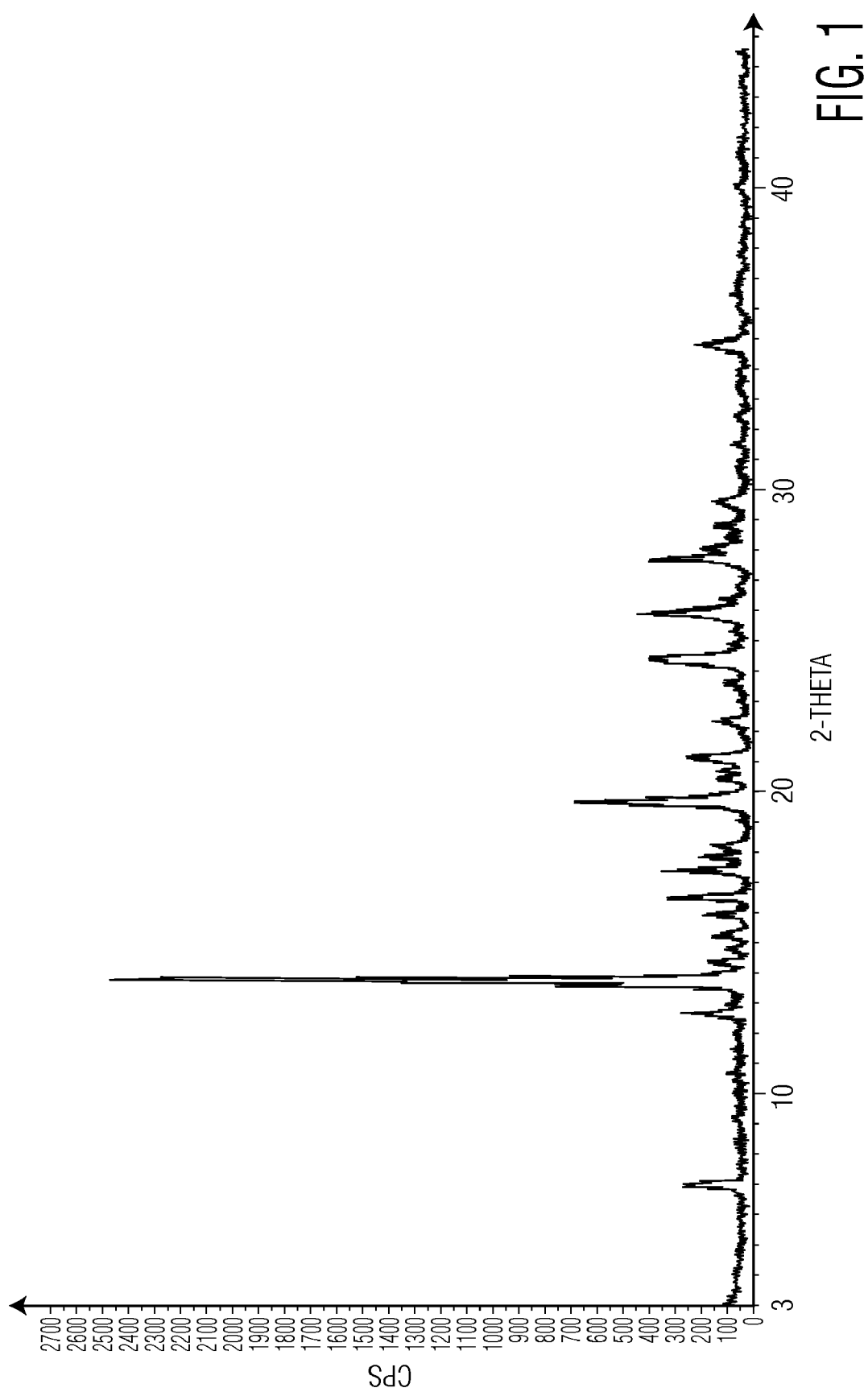
FIG. 1 is an X-ray powder diffraction ("XRPD") pattern for crystalline Form A of voriconazole as prepared in Example 5.

The X-ray diffraction information presented herein is obtained using copper Kα radiation (1.541 Å wavelength). The XRPD patterns show intensity on the vertical axis and the 2θ angle, in degrees, on the horizontal axis.

This invention, in certain aspects, relates to processes for making voriconazole and its different polymorphic forms, including its amorphous form.

In one aspect, the invention provides a process for the preparation of voriconazole of Formula I comprising the steps of:

a) condensation of the compound 1-(2,4-difluorophenyl)-2-(1H-1,2,4-triazole-1-yl)ethanone of Formula II

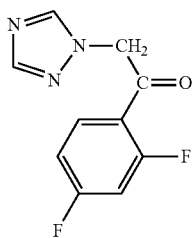

Formula II with the compound 4-chloro-6-ethyl-5-fluoropyrimidine of Formula III

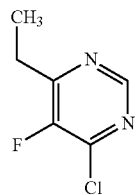

Formula III in the presence of an organolithium derivative in a suitable inert solvent medium to give the compound (2R,3S/2S,3R)-3-(4-chloro-5-fluropyrimidin-6-yl)-2-(2,4-difluropheny1)-1-(1H-1,2,4-triazole-1-yl)butan-2-ol of Formula IV;

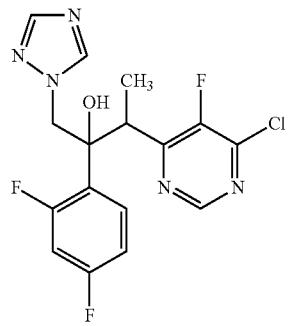

Formula IV b) hydrogenation of the compound of Formula IV in the presence of a noble metal catalyst in a suitable solvent medium to give the racemic compound (2R,3S/2S,3R)-2-(2,4-difluorophenyl)-3-(5-fluoro pyrimidin-4-yl)-1-(1H-1,2,4-triazol-1yl)-butan-2-ol of Formula V;

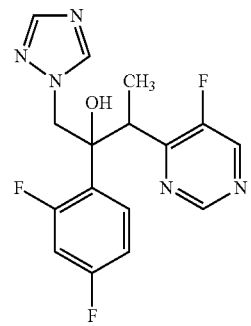

Formula V c) resolution of the racemic compound of Formula V, with R-(−)-10-camphor sulfonic acid in a suitable solvent, to afford the diasteriomeric salt (2R,3S)-2-(2,4-difluorophenyl)-3-(5-fluoropyrimidin-4-yl)-1-(1H-1,2,4-triazol-1yl)butan-2-ol R(−)-10-camphor sulphonate of Formula VI; and

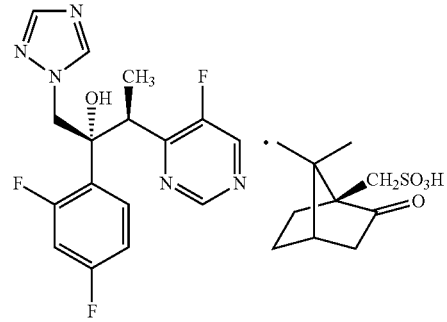

Formula VI d) conversion of the compound of Formula VI to voriconazole by hydrolysis with a suitable base in a suitable solvent.

Step a) involves the condensation of 1-(2,4-difluorophenyl)-2-(1H-1, 2,4-triazole-1-yl) ethanone of Formula II with the compound 4-chloro-6-ethyl-5-fluoropyrimidine of Formula III in the presence of an organolithium derivative in a suitable inert solvent medium to give the compound (2R,3S/2S,3R)-3-(4-chloro-5-fluropyrimidin-6-yl)-2-(2,4-difluropheny1)-1-(1H-1,2,4-triazole-1-yl) -butan-2-ol of Formula IV.

Suitable inert solvents include but are not limited to any solvent or mixture of solvents in which the required components are soluble, such as for example: ethers such as diethyl ether, dimethyl ether, diisopropyl ether, methyl tertiary-butyl ether, tetrahydrofuran, 1,4-dioxane and the like; aliphatic hydrocarbons such as $C_1$-$C_{10}$ straight chain or branched hydrocarbons, and the like; and aromatic hydrocarbons such as toluene, xylene and the like.

Suitable organolithium compounds include $C_1$-$C_6$ alkyl lithium compounds, optionally condensed with amines having one or more $C_1$-$C_6$ alkyl group substituents on a nitrogen atom.

After completion of the condensation, the reaction mass can be quenched by adding a suitable acid such as acetic acid and then diluting with water. After removal of the solid that is produced, such as by filtration, the organic layer of the filtrate can be separated and cooled to form the solid product (2R, 3S/2S,3R)-3-(4-chloro-5-fluoropyrimidin-6-yl)-2-(2,4-difluorophenyl)-1-(1H-1,2,4-triazole-1-yl)-butan-2-ol of Formula IV. No chromatographic separation is needed to recover this product, before it is subjected to further processing.

Suitable temperatures for solid product formation can range from about −40 to 40° C., or about −20 to −0° C., or about −10 to −15° C.

If desired, the solid product can be dried using any technique, such as for example fluid bed drying (FBD), aerial drying, oven drying or other techniques known in the art. The drying can be conducted at temperatures of about 50-100° C. or about 30-40° C., with or without application of vacuum. It is also contemplated that the drying can be carried out under inert atmosphere conditions, if desired.

Step b) involves hydrogenation of (2R,3S/2S,3R)-3-(4-chloro-5-fluoropyrimidin-6-yl)-2-(2,4-difluorophenyl)-1-(1H-1,2,4-triazole-1-yl)-butan-2-ol of Formula IV in the presence of a noble metal catalyst in a suitable solvent medium, to afford the compound (2R,3S/2S,3R)-2-(2,4-difluorophenyl)-3-(5-fluoropyrimidin-4-yl)-1-(1H-1,2,4-triazol-1yl)-butan-2-ol of Formula V.

Examples of the noble metal catalyst that can be used in this process include without limitation Raney™ nickel, platinum, iridium, ruthenium, and the like.

The suitable solvent medium includes but is not limited to alcohol solvents such as $C_{1-10}$ straight chain or branched alcohols, or their mixtures.

The temperatures for conducting the reaction can range from about 20-80° C., or about 30-50° C., or about 40-45° C., under hydrogen pressures ranging from about 2-10 kg/cm$^2$, or about 4-6 kg/cm$^2$.

Step c) involves resolution of racemic compound (2R,3S/2S,3R)-2-(2,4-difluorophenyl)-3-(5-fluoropyrimidin-4-yl)-1-(1H-1,2,4-triazol-1yl)-butan-2-ol of Formula V, with a suitable reagent in a suitable solvent to form the diastereomeric salt (2R,3S)-2-(2,4-difluorophenyl)-3-(5-fluoropyrimidin-4-yl)-1-(1H-1,2,4-triazol-1yl)-butan-2-ol-R-(−)-10-camphor sulphonate of Formula VI.

Suitable reagents that can be used in the resolution reaction of step c) include any chirally active acid which will form salts and separate the isomers. Examples include R-(−)-10-camphor sulfonic acid, L-(−)-mandelic acid, and L-(−)-tartaric acid, and the like.

The solvents useful in this step of the process include solvents such as, for example: ketones such as acetone, ethyl methyl ketone and the like; alcohols such as methanol, ethanol, and isopropanol and like; or their mixtures.

In one embodiment a mixture of a ketone solvent and an alcohol solvent may be used, such as for example acetone and methanol.

Step d) involves conversion of (2R,3S)-2-(2,4-difluorophenyl)-3-(5-fluoro pyrimidin-4-yl)-1-(1H-1,2,4-triazol-1yl)-butan-2-ol-R-(−)-10-camphor sulphonate of Formula VI to voriconazole by the hydrolysis of the compound of Formula VI in a mixture of solvents, such as water and dichloromethane, and in the presence of a base such as aqueous sodium bicarbonate. The layers obtained are separated, the aqueous layer is extracted with a solvent such as dichloromethane, and the combined organic layer is washed with water. The solvent is removed by distillation under vacuum at temperatures below about 70° C. The obtained crude voriconazole is crystallized form isopropyl alcohol to get pure voriconazole.

In another aspect, the present invention provides substantially pure voriconazole and a process for preparation thereof. Voriconazole prepared according to this embodiment has a low level of impurities, as determined by high performance liquid chromatography ("HPLC"). For example, it contains less than about 0.15 area- %, or about 0.05 area- %, of each of the following impurities:

a) 2,4-difluro-1H-1-yl-1,2,4-triazolacetophenone;
b) 6-ethyl-5-fluoropyrimidine;
c) 4-chloro-6-ethyl-5-fluropyrimidine;
d) 6-[(1-(5-fluoropyrimidinyl)-6-ethyl]-4-chloro-5-fluoropyrimidine;
e) (2R,3S/2S,3R)-3-(4-chloro-5-fluoropyrimidin-6-yl)-2-(2,4-difluorophenyl)-1-(1H-1,2,4-triazol-1-yl)-butan-2-ol;
f) (2R,3R/2S,3S)-3-(4-chloro-5-fluoropyrimidin-6-yl)-2-(2,4-difluorophenyl)-1-(1H-1,2,4-triazol-1-yl)-butan-2-ol;
g) (2R,3R/2S,3S)-2-(2,4-difluorophenyl)-3-(5-fluoropyrimidin-4-yl)-1-(1H-1,2,4-triazol-1-yl)-butan-2-ol; and
h) (2S,3R)-2-(2,4-difluorophenyl)-3-(5-fluoropyrimidin-4-yl)-1-(1H-1,2,4-triazol-1-yl)-butan-2-ol.

In general, the voriconazole product purity, as determined by HPLC, will not be less than about 95 area- %, or about 99 area- %, or about 99.5 area-%.

Voriconazole prepared in this process contains residual solvents at concentrations equal to or less than the requirement of ICH guidelines. For example voriconazole prepared according to this process contains the residual solvent acetone at less than about 5000 ppm, or less than about 1000 ppm, or less than about 500 ppm; residual isopropyl alcohol at less than about 5000 ppm, or less than about 1000 ppm, or less than about 500 ppm; and the voriconazole is substantially free from contamination with hexane (LOD: 15 ppm, LOQ: 55 ppm), heptane (LOD: 10 ppm, LOQ: 35 ppm), tetrahydrofuran (LOD: 26 ppm, LOQ: 85 ppm), and methanol (LOD: 30 ppm, LOQ: 100 ppm). The term "LOD" is the approximate limit of detection of an impurity by gas chromatography ("GC") analysis, and the term "LOQ" is the lowest concentration that can be quantified using GC. "Substantially free" means that the concentration of an impurity is less than about twice the LOQ value.

Voriconaozle prepared according to this embodiment has a mean particle size less than about 200 μm, or less than about 100 μm, or less than about 80 μm. This means that about 50 volume percent of the particles have sizes less than, or equal to, the specified size, such as is measured using a laser light scattering instrument.

In yet another aspect, the present invention provides crystalline Form A and Form B of voriconazole and processes for their preparation.

An embodiment of a process for preparing crystalline Form A of voriconazole comprises:

a) suspending voriconazole in a suitable solvent;
b) heating the reaction mass to reflux to obtain a clear solution;

c) cooling the reaction mass to 90-95° C. to allow separation of the voriconazole; and d) separating and washing the solid voriconazole at 90-95° C. with water and then drying by conventional methods to afford crystalline Form A of voriconazole.

The suitable solvent that can be used in step a) includes any solvent or mixture of solvents, in which the required components are soluble. Examples include: alcohols such as $C_1$-$C_{10}$ straight chain or branched alcohols; nitriles such as acetonitrile, propionitrile and the like; ketones such as acetone, methyl ethyl ketene and the like; polar aprotic solvents such as dimethylformamide, dimethylacetamide, dimethylsulfoxide and the like; water; and mixtures thereof.

The separation of solid of step d) can be carried out by using conventional techniques, such as centrifugation, gravity filtration, or vacuum filtration or other techniques known in the art for the separation of solids.

The drying operation of step d) is carried out by using any technique, such as for example fluid bed drying (FBD), air drying, oven drying or other techniques known in the art. The drying can be conducted at temperatures of about 20-100° C. or about 60-70° C. with or without application of vacuum. It is also conceived that the drying could be carried out under inert atmosphere conditions.

The crystalline Form A of voriconazole is characterized by its XRPD pattern substantially in accordance with that shown in FIG. 1. The crystalline Form A of voriconazole is also characterized by its XRPD pattern, wherein the most characteristic peaks are located at about 6.9, 9.2, 10.7, 12.7, 13.7, 13.9, 14.4, 14.84, 15.3, 19.8, 20.8, and 27.0, ±0.2 degrees two theta.

Figure 2:
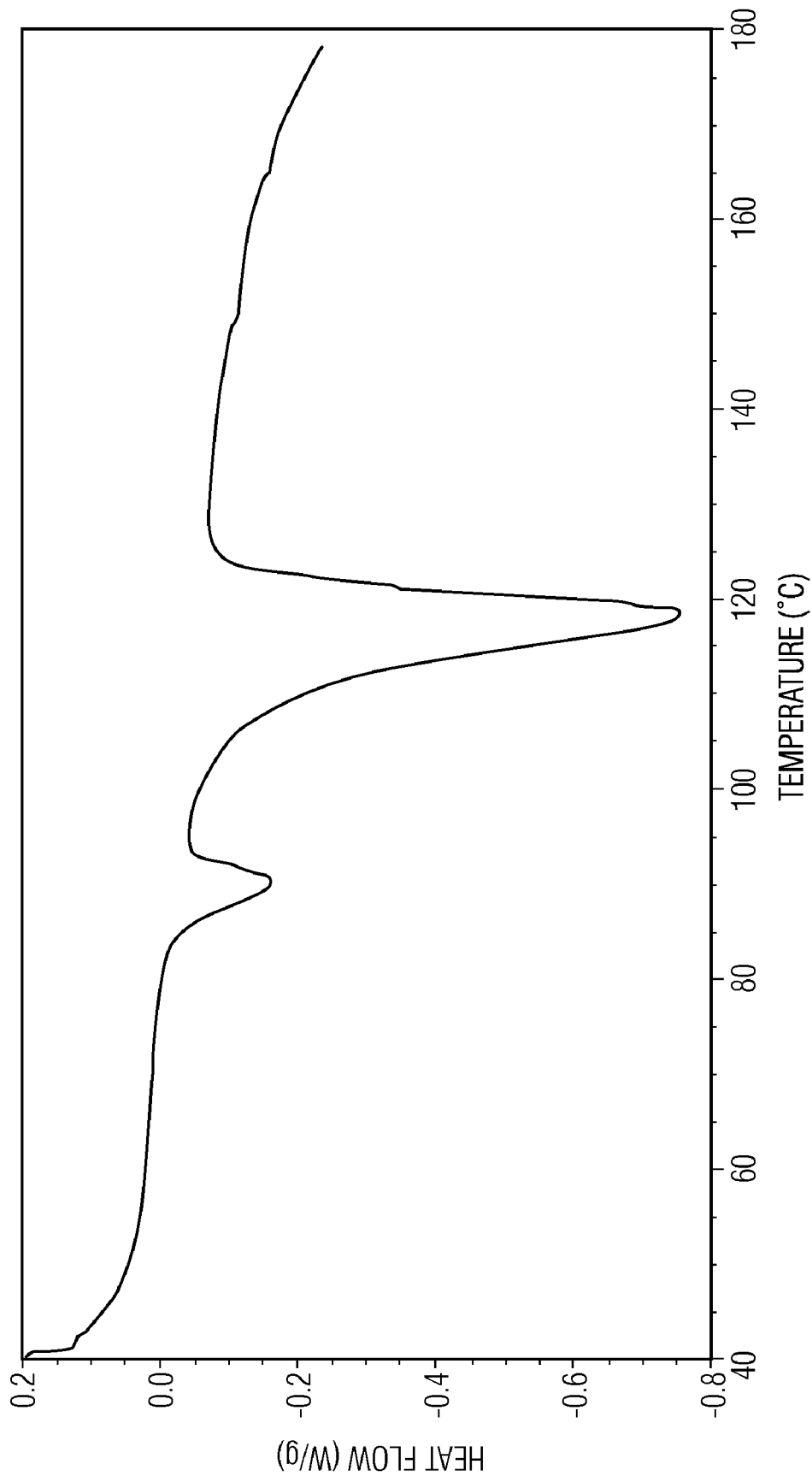
FIG. 2 is a differential scanning calorimetry curve for crystalline Form A of voriconazole as prepared in Example 5.

The crystalline Form A of voriconazole is also characterized by a differential scanning calorimetric pattern substantially in accordance with that depicted in FIG. 2. The crystalline Form A of voriconazole is also characterized by a differential scanning calorimetry curve having endotherms at about 90.4° C. and 118.5° C.

Figure 3:
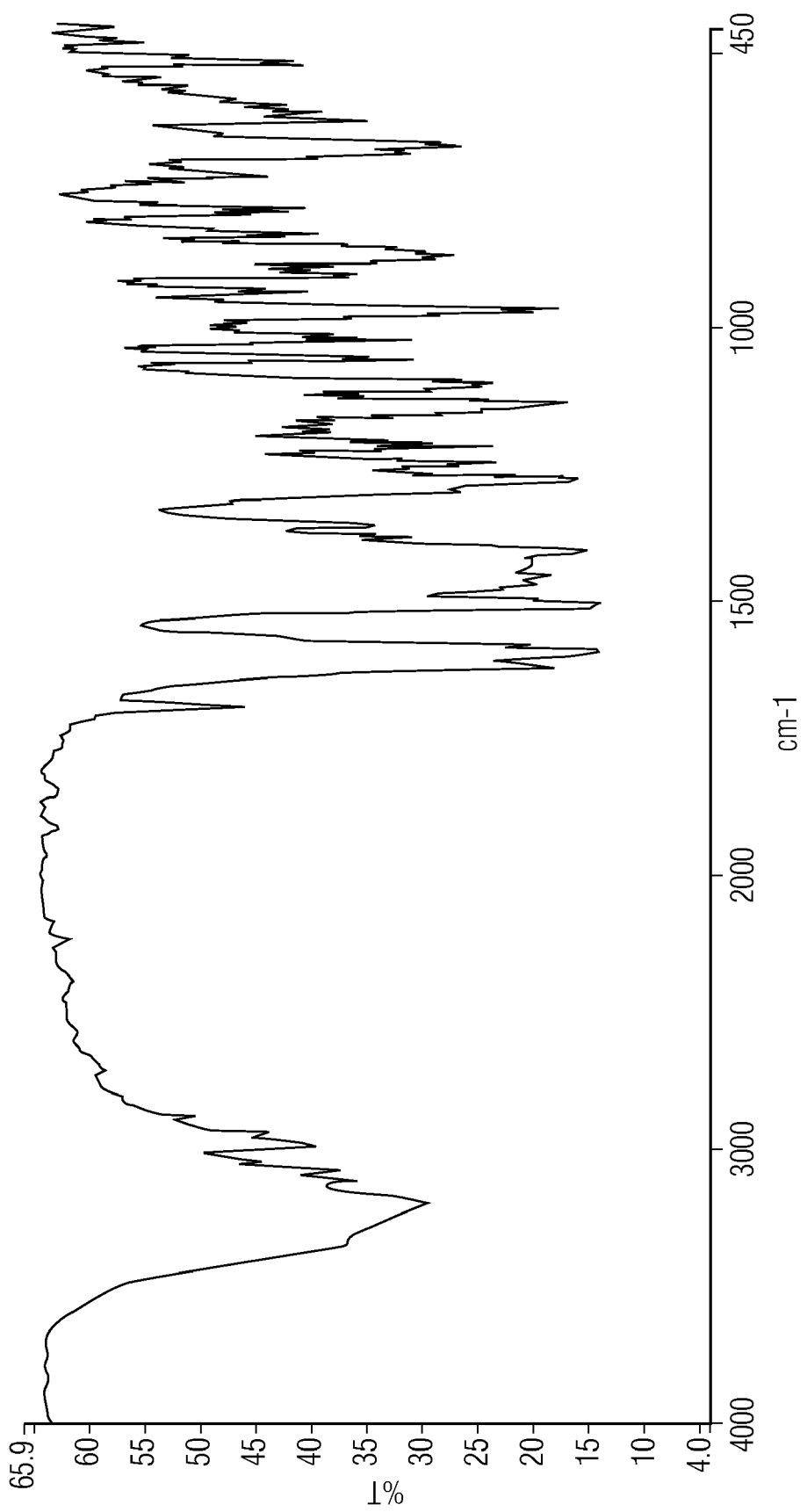
FIG. 3 is an infrared absorption spectrum of crystalline Form A of voriconazole as prepared in Example 5.

The crystalline Form A of voriconazole is also characterized by an infrared absorption spectrum substantially in accordance with that shown in FIG. 3.

According to another aspect, an embodiment of a process for the preparation of crystalline Form B of voriconazole is provided which comprises:

a) providing a solution of voriconazole in a suitable solvent(s);

b) precipitating the solid by adding water at reflux temperature;

c) cooling the solution;

d) isolation of the precipitated solid; and e) drying the solid compound of step (d) to get Form B of voriconazole The step of providing a solution of voriconazole may include dissolving any form of voriconazole in a suitable organic solvent or obtaining an existing solution from a previous processing step.

A suitable solvent that can be used in step a) includes any solvent or mixture of solvents. Examples include ketones such as acetone, methyl ethyl ketone, methyl isobutyl ketone and the like.

The dissolution temperature may range from about 0 to 100° C. or about 20 to 50° C. or about 25 to 30° C. or at the reflux temperature of the solvent used. Any temperature can be chosen as long as a clear solution of voriconazole in the solvent(s) is formed and the stability of the voriconazole is not compromised.

The reaction mass of step b) can be cooled to a temperature that may range from about 0 to 50° C. or about 25 to 30° C.

The isolation of solid of step d) can be carried out by using conventional techniques, such as centrifugation, gravity filtration, or vacuum filtration or other techniques known in the art for the separation of solids.

The drying operation of step e) is carried out by using any technique, such as for example fluid bed drying (FBD), aerial drying, oven drying or other techniques known in the art. The drying can be conducted at temperatures of about 20-100° C. or about 60-70° C. with or without application of vacuum. It is also conceived that the drying could be carried out under inert conditions.

An embodiment of an alternative process for the preparation of crystalline Form B of voriconazole comprises:

a) providing a solution of voriconazole in a suitable solvent;

b) cooling the solution for solid separation.

c) isolation of the solid; and d) optionally, drying the solid to get Form B of voriconazole The step of providing a solution of voriconazole may include dissolving any form of voriconazole in a suitable organic solvent or obtaining an existing solution from a previous processing step, such as the final step in a voriconazole synthesis.

A suitable solvent that can be used in step a) includes any solvent or mixture of solvents, in which voriconazole is soluble. Examples include: chlorohydrocarbons such as dichloromethane, ethylene dichloride, chloroform and the like; nitriles such as acetonitrile, propionitrile and the like; alcohols such as methanol, ethanol, isopropanol and the like; ketones such as acetone methyl ethyl ketone, methyl isobutyl ketone and the like; ethers such as tetrahydrofuran, 1,4-dioxane and the like; or mixtures thereof.

The dissolution temperature may range from about 0 to 100° C., or about 20 to 50° C., or about 25 to 30° C., or at the reflux temperature of the solvent used. Any temperature can be chosen as long as it results in a clear solution of voriconazole in the solvent or mixture of solvents and the stability of the voriconazole is not compromised.

The solution of step a) can be cooled to a temperature that may range from about 20 to 50° C., or about 25 to 30° C., or at a temperature where the voriconazole is precipitated.

The isolation and drying operations can be carried out as described above for the previous process for preparing Form B.

Figure 4:
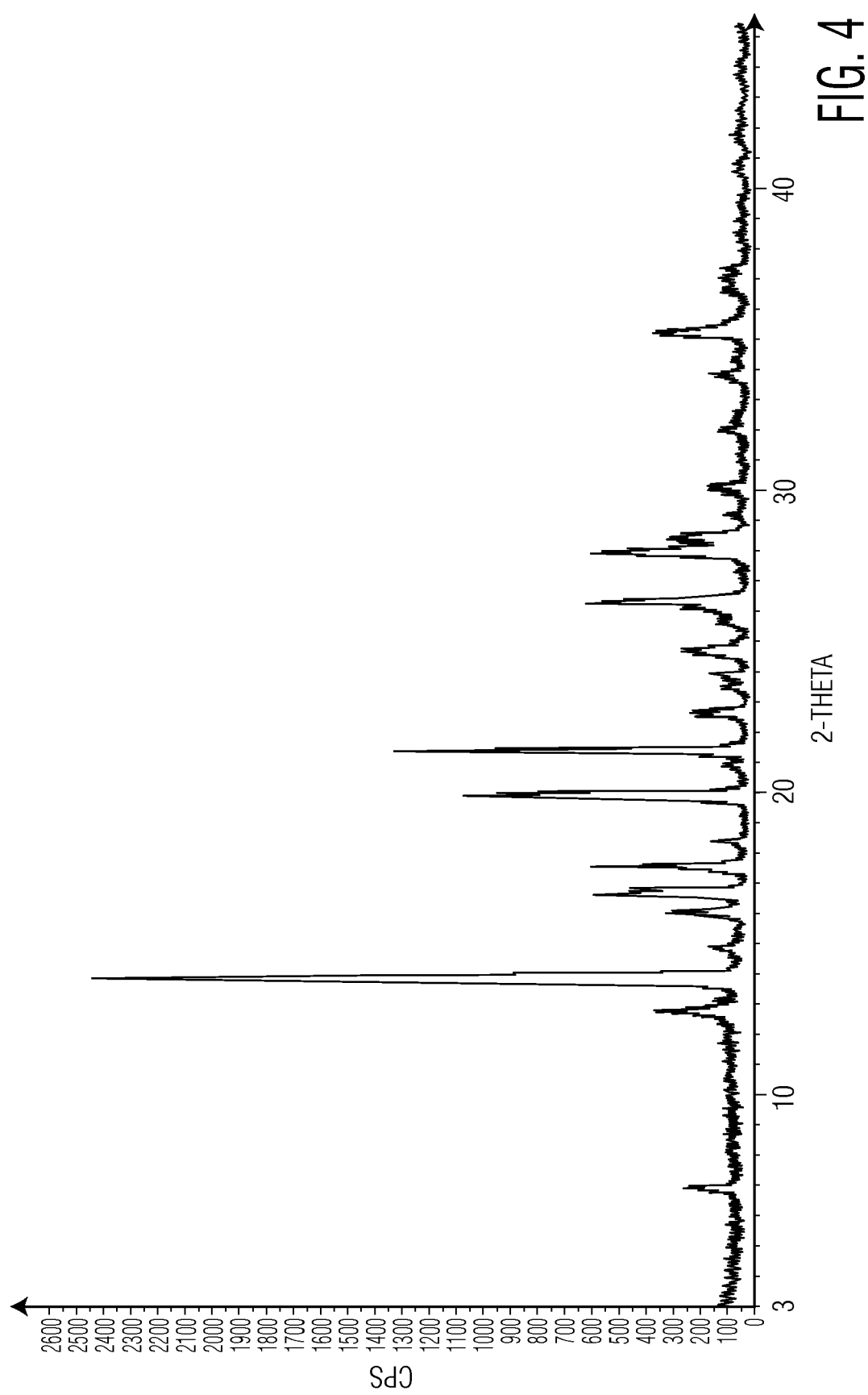
FIG. 4 is an X-ray powder diffraction pattern for the crystalline Form B of voriconazole as prepared in Example 7.

The crystalline Form B of voriconazole is characterized by its XRPD pattern substantially in accordance with that shown in FIG. 4. The crystalline form B of voriconazole is also characterized by its XRPD pattern, wherein the most characteristic peaks are located at about 6.9, 12.6, 13.8, 14.8, 15.9, 16.5, 17.4, 19.8, 21.2, 22.5, 23.3, 26.1, and 27.8±0.2 degrees two theta.

Figure 5:
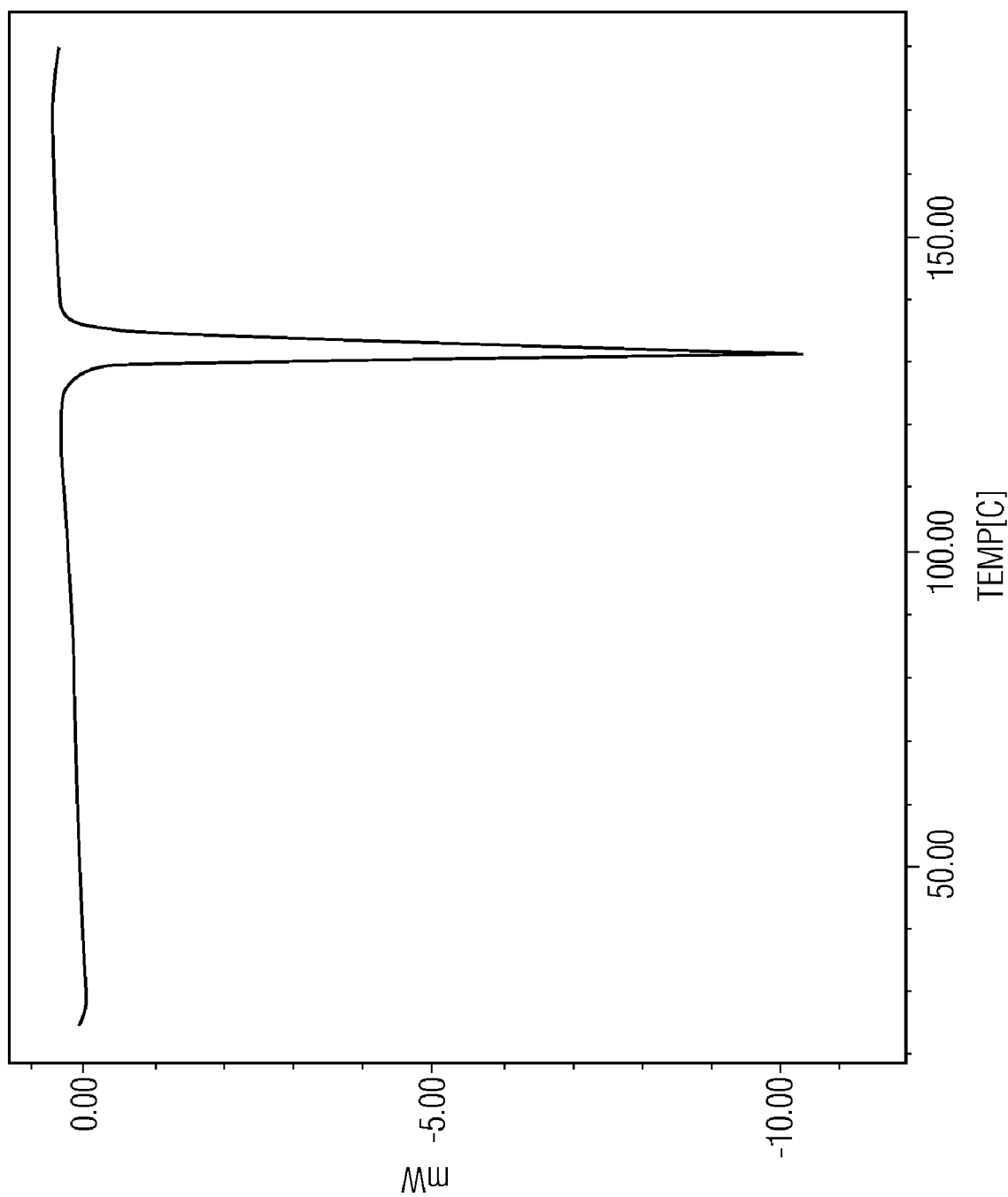
FIG. 5 is a differential scanning calorimetry curve for crystalline Form B of voriconazole as prepared in Example 7.

The crystalline Form B of voriconazole is also characterized by its differential scanning calorimetry curve substantially in accordance with that shown in FIG. 5. The crystalline Form B of voriconazole is also characterized by a differential scanning calorimetry curve having an endotherm at about 130.9° C.

Figure 6:
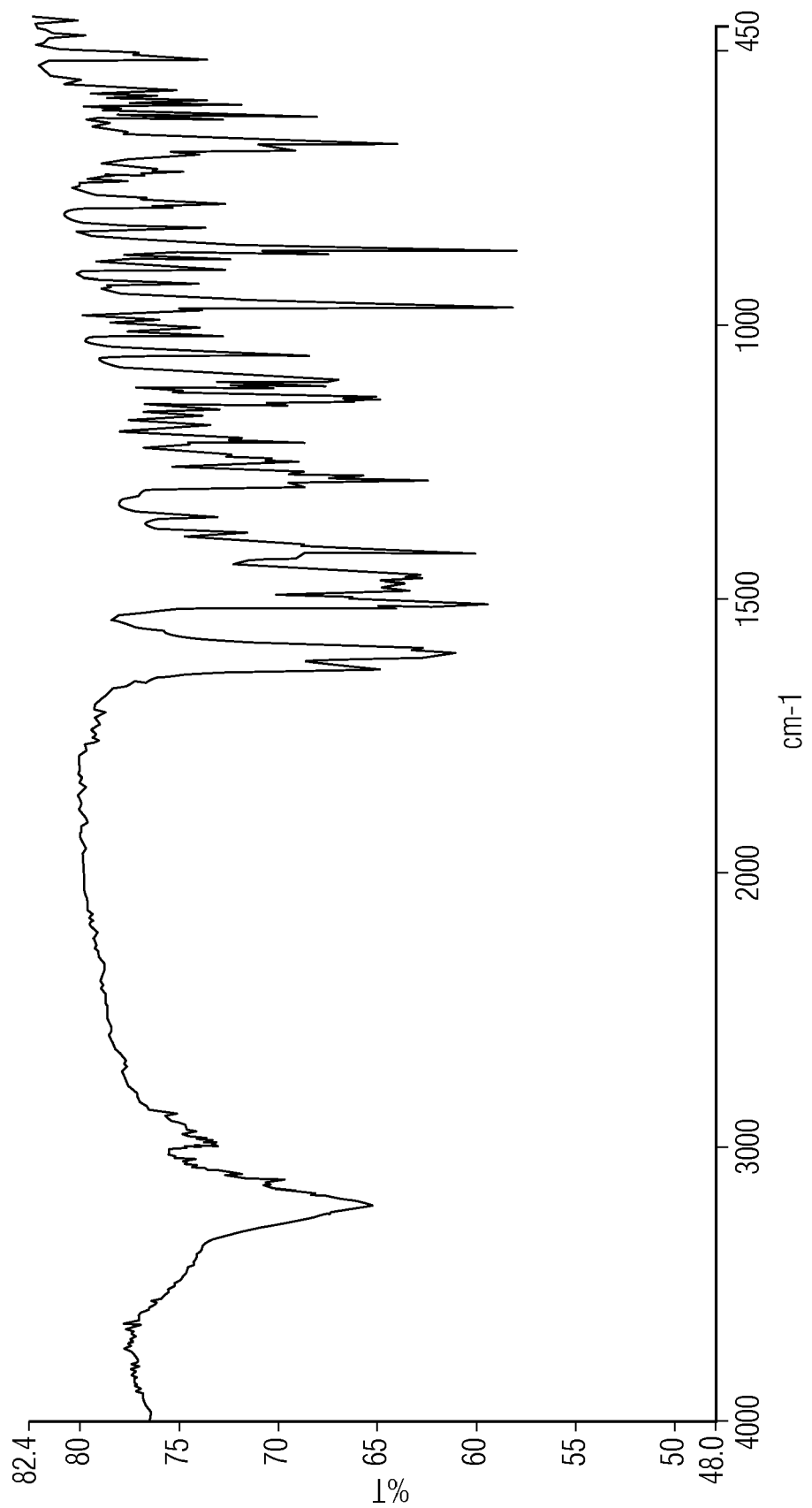
FIG. 6 is an infrared absorption spectrum of crystalline Form B of voriconazole as prepared in Example 7.
Figure 7:
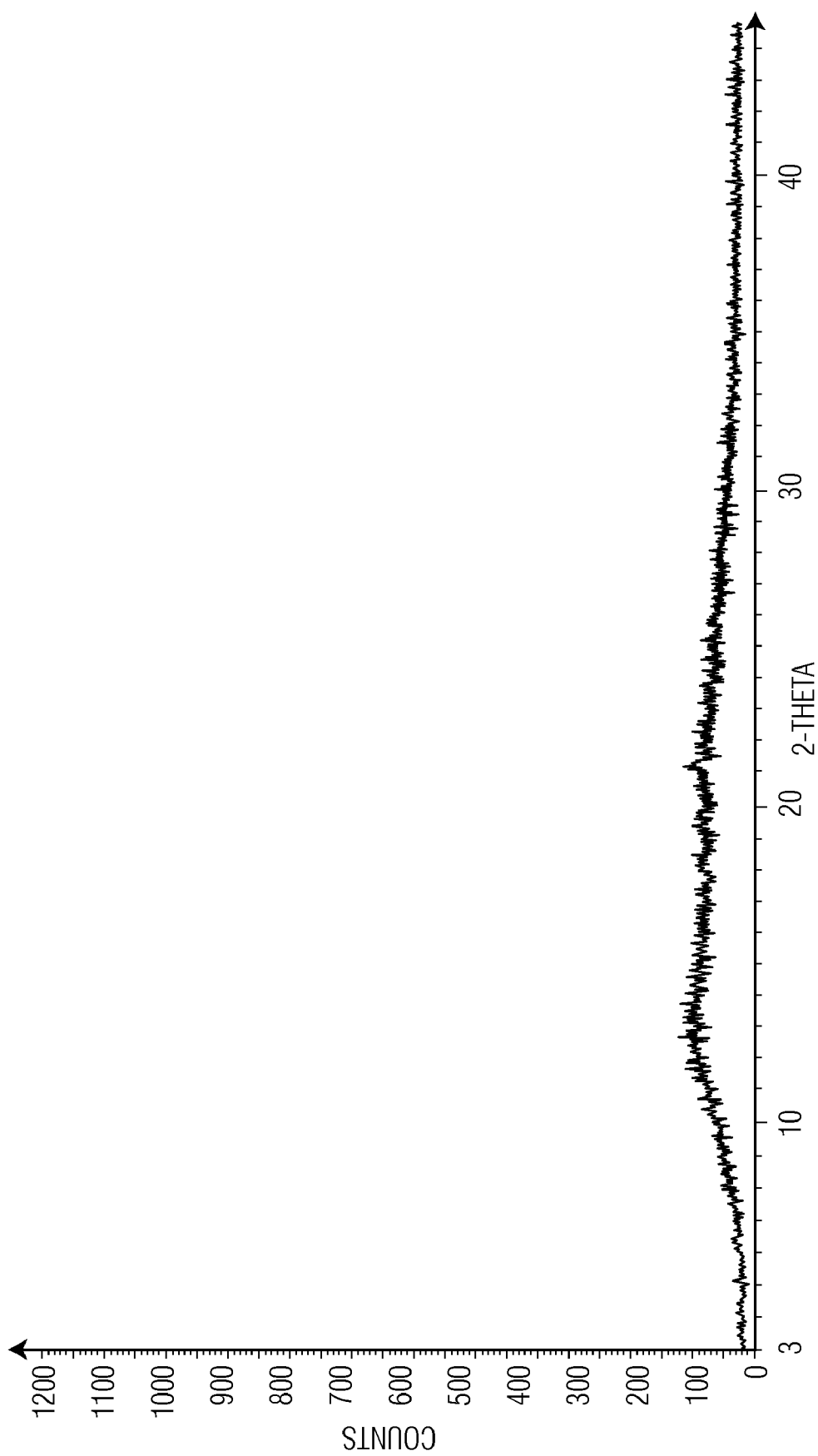
FIG. 7 is an X-ray powder diffraction pattern for the amorphous voriconazole as prepared in Example 10.

The crystalline Form B of voriconazole is also characterized by an infrared absorption spectrum substantially in accordance with that shown in FIG. 6.

Any form of voriconazole may be used for the preparation of the solutions resulting in the formation of either Form A or B according to the processes of the invention.

In a still further aspect, the present invention provides an amorphous voriconazole in combination with a pharmaceutically acceptable carrier, and a process for its preparation.

An embodiment of a process for preparing an amorphous voriconazole composition comprises:

a) providing a solution of voriconazole and a pharmaceutically acceptable carrier in an organic solvent;

b) removing the solvent to obtain a solid residue which is comprises an amorphous form of voriconazole.

The step of providing a solution of voriconazole and a pharmaceutically acceptable carrier may include dissolving any form of voriconazole and a pharmaceutically acceptable carrier in a suitable organic solvent, or obtaining an existing solution of voriconazole from a previous processing step, such as a final step in a voriconazole synthesis, and dissolving a pharmaceutically acceptable carrier in that solution or adding a solution of a pharmaceutically acceptable carrier in a suitable organic solvent to an existing solution of voriconazole.

The organic solvents that can be used to prepare an amorphous voricanazole composition will be chosen based on the technique used for removal of solvent, the solubility and stability of the voriconazole and the carrier in the solvent and other factors known to a person skilled in the art. The same solvent may be used for the dissolution of the voriconazole and the pharmaceutical carrier or different solvents may be used for the two components and then the solutions mixed together to form a clear homogeneous solution. Examples include: halogenated hydrocarbons such as dichloromethane, ethylene dichloride, chloroform and the like; ketones such as acetone, methyl ethyl ketone, methyl isobutyl ketone and the like; nitriles such as acetonitrile, propionitrile and the like; ethers such as diethyl ether, diisopropyl ether, methyl tertiary butyl ether and the like; esters such as ethyl acetate, propyl acetate and the like; alcohols such as methanol, ethanol, propanol and the like, hydrocarbons such as $C_1$-$C_6$ straight chain, branched, or cyclic hydrocarbons and the like; or mixtures thereof.

The pharmaceutical carriers that can be used for preparing amorphous voriconazole compositions include, but are not limited to: hydrophilic carriers like polymers of N-vinylpyrrolidone commonly known as polyvinylpyrolidine ("PVP" or "povidone"); gums; cellulose derivatives; cyclodextrins; gelatins; hypromellose phthalate; sugars; polyhydric alcohols; polyethylene glycols; polyethylene oxides; polyoxyethylene derivatives; polyvinyl alcohol; propylene glycol derivatives; and the like.

Pyrrolidones that are useful in the practice of this invention are homopolymers or copolymers of N-vinylpyrrolidone. Such polymers are known to form complexes with a variety of compounds. The water-soluble forms of N-vinylpyrrolidone are available in a variety of viscosity and molecular weight grades and may be chosen from but are not limited to PVP K-12, PVP K-15, PVP K-17, PVP K-25, PVP K-30, PVP K-120, and the like. A water-insoluble N-vinylpyrrolidone can be a cross-linked PVP such as, for example, crospovidone. Any of these PVPs may be chosen, or their mixtures, or their mixtures with any of the other carriers mentioned above.

Any pharmaceutical carrier is acceptable as long as it allows the preparation of the amorphous voriconazole as described herein, is compatible with the voriconazole and is acceptable for human use. The choice of such a carrier is within the scope of understanding of a person skilled in the art and is not limited by the list of polymers and excipients provided above.

The dissolution temperatures may range from about 0 to 125° C., or about 20 to 50° C., or about 25-30° C., or at the reflux temperature of the solvent used. Any temperature can be chosen as long as the stability of the voriconazole and the pharmaceutically acceptable carrier is not compromised.

The ratio of the pharmaceutically acceptable carrier to the voriconazole can include any proportions as long as the required amorphous voriconazole is obtained. The solvent can be removed from the solution using distillation under vacuum, or spray drying, or agitated thin film drying. The solvent can also be removed from the solution using other techniques known in art, including, for example, distillation, evaporation, oven drying, tray drying, rotational drying (such as using the Buchi Rotavapor), freeze-drying, fluidized bed drying, flash drying, spin flash drying, and the like.

The process may include optionally further drying of the product obtained from the solution by known drying methods, as will be apparent to the skilled artisan.

The amorphous form of voriconazole of the present invention is characterized by a diffuse halo in its XRPD pattern, which is substantially as shown in FIG. 8.

In yet another aspect, the present invention provides pharmaceutical compositions containing the substantially pure voriconazole either as one or more of crystalline form A, form B or amorphous voriconazole either alone or in amorphous combination with pharmaceutically acceptable excipients and processes for the preparation thereof.

Raney™ nickel is a sponge-metal catalyst produced when a block of nickel-aluminum alloy is treated with concentrated sodium hydroxide. Raney™ is a registered trademark of W. R. Grace and Company.

The substantially pure voriconazole obtained according to the processes of the invention or any of the polymorphic forms of this voriconazole are all useful in the preparation of pharmaceutical compositions for the treatment of a variety of disease conditions. Such conditions include for example without limitation, invasive aspergilli; treatment of fluconazole-resistant, severe, invasive candida infections (including *C. krusei*); and treatment of severe fungal infections involving *scedosporium* spp. and *Fusarium* spp. Other medical conditions where voriconazole could be utilized for treatment or prophylaxis are completely within the scope of the invention.

Such pharmaceutical compositions can include without limitation, solid oral formulations such as tablets, capsules, powders, granules, and the like, suspensions, injectable compositions, and other forms of drug delivery where voriconazole would find use. Suitable excipients required for the processing of the voriconazole and converting it into the final composition are within the scope of understanding of a person skilled in the art of preparing pharmaceutical compositions for drug delivery.

The dose administration of the compositions prepared from the voriconazole forms of the invention will be determined by the medical practitioner.

Certain aspects and embodiments of the processes and forms described herein are further described in the following examples. These examples are provided solely for the purpose of illustrating particular aspects and embodiments of the invention, and therefore should not be construed as limiting the scope of the invention.

EXAMPLE 1

Preparation of (2R,3S/2S,3R)-3-(4-Chloro-5-Fluropyrimidin-6-yl)-2-(2,4-Difluorophenyl)-1-(1H-1,2,4-Triazole-1-yl)Butan-2-ol (Formula IV)

1258 g of diisopropylamine was charged into a reactor containing a mixture of n-heptane (15 L) and tetrahydrofuran (2 L), under a nitrogen atmosphere and cooled to about −18 to −23° C. 27.9 g of n-butyl lithium (1.6 molar solution in hexanes) was added dropwise, while maintaining the temperature at −18 to −23° C. The reaction mixture was stirred for about 2 hours at the same temperature and then cooled to about −65 to −70° C. 7.5 kg of 4-chloro-6-ethyl-5-fluoropyrimidine was added at about −69 to −73° C. over about 15 minutes. 20.8 kg of 2,4-difluoro-1H-1-yl-1,2,4-triazolacetophenone was dissolved in 60 L of tetrahydrofuran in another vessel at about 50-55° C. and filtered through paper to remove extraneous particulate matter. This filtered solution was added slowly to the reaction mass at −68 to −74° C. over a period of about 2 hours and maintained at −68 to −74° C. for about 3 hours. 7.5 L of acetic acid was added slowly to the reaction mass at −57 to −69° C. after confirming the reaction completion by thin layer chromatography. 75 L of water was added at below −10° C. and then the temperature was raised to about 10-15° C. The suspension was filtered through cloth at 10-15° C. and washed with 7.5 L of n-heptane. The organic layer was separated from the resultant filtrate and washed with a total of 240 L water in four portions. The organic layer was gradually cooled to about −10 to −15° C., and stirred for about 90 minutes. The separated solid was filtered and washed with 7.5 L of n-heptane. Obtained solid was dried at 35-40° C. under vacuum (about 600 mm Hg) for about 6 hours to yield 4.6 kg of the title compound as a crystalline solid. (Yield: 26.3%)

EXAMPLE 2

Preparation of (2R, 3S/2S, 3R)-2-(2,4-Difluorophenyl)-3-(5-Fluoro Pyrimidin-4-yl)-1-(1H-1, 2,4-Triazol-1yl)Butan-2-ol (Formula V)

4.3 kg of (2R,3S/2S,3R)-3-(4-chloro-5-fluropyrimidin-6-yl)-2-(2,4-diflurophenyl)-1-(1H-1,2,4-triazole-1-yl)butan-2-ol was charged into a stainless steel autoclave reactor containing 26 L of methanol. 1100 g of sodium acetate and 860 g of Raney™ nickel were charged and a 3 kg/cm² hydrogen pressure was applied. The reaction mass was heated to about 54-56° C., and maintained for about 5 hours at 4-5 kg/cm² hydrogen pressure. Reaction completion was confirmed by thin layer chromatography and the mixture was cooled to 25-35° C. The catalyst was recovered by vacuum filtration and washed with 9 L of methanol. The filtrate was charged into the reactor and solvent was removed by distillation under reduced pressure of about 650 mm Hg at below 45° C. until a thick compound separated. Cooled the reaction mass to about 33° C. and 19.5 L of water was added. Reaction suspension was stirred for 10 minutes and then gradually cooled to about 5-10° C. and stirred for about 2 hours. The separated solid was filtered and was washed with chilled water (4 L). Obtained solid was dried at 55-60° C. for about 6 hours to yield 2.6 kg of the title compound in the form of a crystalline solid. (Yield: 66.4%)

EXAMPLE 3

Preparation of (2R,3S)-2-(2,4-Difluorophenyl)-3-(5-Fluoro Pyrimidin-4-yl)-1-(1H-1,2,4-Triazol-1yl)Butan-2-ol-R-(−)-10-Camphor Sulphonate Salt (Formula VI)

2.5 kg of (2R,3S)-2-(2,4-difluorophenyl)-3-(5-fluoropyrimidin-4-yl)-1-(1H-1,2,4-triazol-1yl)butan-2-ol was charged into a reactor containing 25 L of acetone. 1.65 kg of R-(−)-10-camphor sulphonic acid was added and heated to about 50° C. 12.5 L of methanol was added to the reaction mass to make a clear solution. It was then heated to reflux and maintained for 20 minutes. The reaction mass was then cooled to about 30° C. and maintained for about 1 hour. The separated solid was centrifuged and washed with 2.5 L of chilled acetone. The obtained solid was dried at about 55-60° C. under a vacuum of about 650 mm Hg for about 8 hours to yield 1.35 kg of the title compound as a crystalline solid. (Yield: 65.0%)

EXAMPLE 4

Preparation of (2R,3S)-2-(2,4-Difluorophenyl)-3-(5-Fluoro Pyrimidin-4-yl)-1-(1H-1,2,4-Triazol-1yl) Butan-2-ol (Voriconazole)

4.9 kg of (2R, 3S)-2-(2,4-difluorophenyl)-3-(5-fluoropyrimidin-4-yl)-1-(1H-1,2,4-triazol-1yl)butan-2-ol-R-(−)-10-camphor sulfonate salt was charged into a reactor containing 10 L of water and 25 ml of dichloromethane. Reaction mass pH was adjusted to about 10 with 20% sodium carbonate solution (10 L) at room temperature. Stirred the reaction mass for 20 minutes. The aqueous layer was separated and extracted with dichloromethane (5 L). Combined organic layer was washed with water 2.5 L each of in two portions. 0.25 kg of activated charcoal was added to the organic layer and stirred for 5 minutes. Filtered the carbon through a candle filter and washed with 2.5 L of dichloromethane. The solvent was distilled completely in an agitated thin film dryer ("ATFD") under vacuum of about 600 mm Hg at below 40° C. The solid material thus obtained from the ATFD was charged into a reactor containing 17.5 L of isopropyl alcohol. Reaction mass was heated to 59.5° C. and maintained for 15 minutes to form a clear solution. The solution was cooled to about 5° C. and stirred for 1 hour and 15 minutes at 2-5° C. The separated solid was centrifuged and washed with 2.5 L of chilled isopropyl alcohol. Obtained solid was dried at about 57-60° C. for about 7 hours and 20 minutes to yield 2.28 kg of the title compound as a crystalline solid. (Yield: 76%, Purity: 99.96% by HPLC, crystalline Form B).

EXAMPLE 5

Preparation of Voriconazole Crystalline Form A 5 g of voriconazole and 15 ml of water were charged into a round bottom flask and heated to reflux to get a clear solution. Reaction mass was cooled to 90-95° C. for compound separation and was filtered at 90-95° C. The obtained solid was dried at 60-70° C. to afford 4.1 g of the title compound.

EXAMPLE 6

Preparation of Voriconazole Crystalline Form B (2R,3S)-2-(2,4-difluorophenyl)-3-(5-fluoropyrimidin-4-yl)-1(1H-1,2,4-triazol-1-yl)-butan-2-ol-R(−)-10-camphor sulphonate (4 g), water (11 ml) and dichloromethane (19 ml) were charged into a round bottom flask. Reaction mass pH was adjusted to 11-12 with 10% sodium hydroxide solution (4 ml). The organic layer was separated from the aqueous layer and the aqueous layer was extracted with dichloromethane (4 ml). Combined organic layers were washed with water (3×11 ml). Solvent from the organic layer was removed completely under reduced pressure at below 45° C. Acetone (12 ml) was added to the residue and was stirred for about 15 minutes at 25-35° C. Solvent was removed completely under reduced pressure at below 45° C. to form a residue. Acetone (20 ml) was added to the residue and the mixture was heated to reflux.

Water (80 ml) was slowly added into the mixture at reflux for the precipitation of the compound. The mixture was cooled to 40° C. and was maintained at 40° C. for about 30 minutes. The separated solid was collected by filtration and was washed with water (4 ml). The obtained solid was dried at about 60° C. for about 3 hours to afford 1.3 g of the title compound.

EXAMPLE 7

Alternate Preparation of Voriconazole Crystalline Form B

A mixture of polymorphs of (2R,3S)-2-(2,4-difluorophenyl)-3-(5-fluoropyrimidin-4-yl)-1(1H-1,2,4-triazol-1-yl)butan-2-ol (voriconazole) (20 g) and acetone (80 ml) were charged into a round bottom flask and was heated to reflux. Water (240 ml) was added to the mixture at reflux. The mixture was cooled to 40° C. and was maintained for about 60 minutes at 40° C. The separated solid was filtered and was washed with water (20 ml) and was dried at about 60° C. to afford 11.6 g of the title compound.

EXAMPLE 8

Alternate Preparation of Voriconazole Crystalline Form B 5 g of voriconazole and methanol (20 ml) were charged into a round bottom flask and stirred for 10 minutes. The mixture was then cooled to about 0° C. and was maintained at 0° C. for about 30 minutes. The separated solid was filtered and was washed with chilled methanol (5 ml). The obtained solid was dried at about 60° C. to afford 1.4 g of the title compound.

EXAMPLE 9

Alternate Preparation of Voriconazole Crystalline Form B 5 g of voriconazole and acetonitrile (5 ml) were charged into a round bottom flask and heated to reflux to get a clear solution. The solution was cooled to 25-35° C. and was maintained for about 30 minutes. The separated solid was filtered and washed with acetonitrile (5 ml). The obtained solid was dried at about 52° C. for about 6 hours to afford 1.0 g of the title compound.

EXAMPLE 10

Preparation of Amorphous Voriconazole Composition 2.5 g of voriconazole and povidone (PVP K-30, 2.5 g) were suspended in methanol (20 ml) at 25-30° C. and stirred for about 15 minutes to obtain a clear solution. Distilled the solvent to dryness in a Buchi Rotavapor at 50-55° C. under a vacuum of 500-600 mm Hg, followed by drying the solid obtained at 50-55° C. under a vacuum of 700-750 mm Hg for about 60 minutes to afford 4.8 g of the desired amorphous voriconazole composition.

EXAMPLE 11

Preparation of Amorphous Voriconazole Composition

Voriconazole (2.5 g) and povidone (PVP K-30, 2.5 g) were suspended in dichloromethane (15 ml) at 25-30° C. and stirred for about 10 minutes to obtain a clear solution. Distilled the solvent to dryness in a Buchi Rotavapor at 30-40° C. under a vacuum of 550-700 mm Hg for about 2 hours, to afford 5.0 g of the desired amorphous voriconazole composition.

The amorphous voriconazole composition had the following properties:

Bulk density: 0.46 g/ml (without tapping), 0.72 g/ml (after tapping).
Hausner ratio: 1.56.
Carr Compressibility Index: 36.4%.
Angle of repose: 39.35 degrees.
Stability (under accelerated conditions: 75% relative humidity and 40° C.): converts to a crystalline form after 5 days, moisture uptake 11% by weight.

Solubility comparison at room temperature (values in mg/l):

| Solvent | Amorphous | Crystalline Form B |
|---|---|---|
| Methanol | 167 | 125 |
| Acetone | 250 | 250 |
| Water | 0 | 0 |

EXAMPLE 12

Preparation of Amorphous Voriconazole Composition by Spray Drying

Voriconazole (5.0 g) and povidone (PVP K-30, 5.0 g) were suspended in methanol (40 ml) at 25-30° C. and stirred for 10 minutes to obtain a clear solution. The solvent was removed using a spray drier under the following set of conditions: feed pump 10 rpm; aspirator 1000 rpm; inlet air temperature 80° C.; outlet air temperature, 38° C.; $N_2$ pressure, 2 kg/cm$^2$; feed temperature, room temperature; to afford 4.5 g of the desired voriconazole amorphous composition.

EXAMPLE 13

Preparation of Amorphous Voriconazole Composition by Agitated Thin Film Drying

Voriconazole (50 g) and povidone (PVP K-30, 50 g) were suspended in methanol (400 ml) at 25-30° C. and stirred for about 15 minutes to obtain a clear solution. The solvent was removed using an agitated thin film dryer at a feed rate of 10 L/hour, under a vacuum of 650-700 mm Hg, and a jacket temperature of about 65° C., to afford 88.0 g of the desired voriconazole amorphous composition.

The invention claimed is:

1. A process for hydrogenating (2R,3S/2S,3R)-3-(4-chloro-5-fluropyrimidin-6-yl)-2-(2,4-diflurophenyl)-1-(1H-1,2,4-triazole-1-yl)butan-2-ol to give (2R,3S/2S,3R)-2-(2,4-difluorophenyl)-3-(5-fluoropyrimidin-4-yl)-1-(1H-1,2,4-triazol-1-yl)butan-2-ol comprising using Raney™ nickel as catalyst.

2. The process of claim 1, further comprising resolving the (2R,3S/2S,3R)-2-(2,4-difluorophenyl)-3-(5-fluoro pyrimidin-4-yl)-1-(1H-1,2,4-triazol-1yl)butan-2-ol to afford a diastereomeric salt of (2R,3S)-2-(2,4-difluorophenyl)-3-(5-fluoropyrimidin-4-yl)-1-(1H-1,2,4-triazol-1yl)butan-2-ol.

3. The process of claim 2, wherein resolving comprises reacting (2R,3S/2S,3R)-2-(2,4-difluorophenyl)-3-(5-fluoro pyrimidin-4-yl)-1-(1H-1,2,4-triazol-1-yl)butan-2-ol with a chirally active acid to form a diastereomeric salt.

4. The process of claim 3, wherein the chirally active acid is selected from the group consisting of R-(-)-camphor sulfonic acid, L-(-) mandelic acid, and L-(-) tartaric acid.

5. The process of claim 2, further comprising converting the diastereomeric salt to voriconazole.

6. The process of claim 1, wherein the (2R,3S/2S,3R)-3-(4-chloro-5-fluoropyrimidin-6-yl)-2-(2,4-diflurophenyl)-1-(1H-1,2,4-triazole-1-yl)butan-2-ol is obtained by condensing 1-(2,4-difluorophenyl)-2-(1H-1,2,4-triazole -1-yl) ethanone with 4-chloro-6-ethyl-5-fluoropyrimidine, in a combination of an ether and an aliphatic hydrocarbon solvent.

7. The process of claim 6, wherein condensing is conducted in the presence of an organolithium derivative.

8. The process of claim 7, wherein condensing is conducted in the presence of a $C_1$-$C_6$ alkyl lithium compound, optionally condensed with an amine having one or more $C_1$-$C_6$ alkyl group substituents on a nitrogen atom.

9. The process of claim 8, wherein condensing is conducted in the presence of a $C_1$-$C_6$ alkyl lithium compound.

10. The process of claim 8, wherein condensing is conducted in the presence of a $C_1$-$C_6$ alkyl lithium compound, condensed with an amine having one or more $C_1$-$C_6$ alkyl group substituents on a nitrogen atom.

* * * * *